United States Patent [19]

Teutsch et al.

[11] Patent Number: 4,753,932
[45] Date of Patent: Jun. 28, 1988

[54] NOVEL 10-SUBSTITUTED STEROIDS

[75] Inventors: Jean-Georges Teutsch, Pantin; Germain Costerousse, Saint-Maurice; Vesperto Torelli, Maisons-Alfort; Daniel Philibert, La Varenne Saint Hilaire, all of France

[73] Assignee: Roussel Uclaf, Paris, France

[21] Appl. No.: 818,884

[22] Filed: Jan. 14, 1986

[30] Foreign Application Priority Data

Jan. 14, 1985 [FR] France .................. 85 00434

[51] Int. Cl.$^4$ .............. A61K 31/56; A61K 31/58; C07J 1/00; C07J 43/00
[52] U.S. Cl. .................. 514/179; 514/172; 514/176; 260/397.45; 540/113
[58] Field of Search .......... 514/172, 176, 179; 260/397.45; 540/113

[56] References Cited

U.S. PATENT DOCUMENTS 3,132,138 5/1964 Nomine et al. ............ 260/239.5

FOREIGN PATENT DOCUMENTS 0188396 7/1986 European Pat. Off. .......... 514/179
8303099 9/1983 PCT Int'l Appl. .

OTHER PUBLICATIONS

Steroids–Experimental Section; Patrick A. Marcotte & Cecil H. Robinson "Synthesis and Evaluation of 10--Substituted 4-Esterene-3,17-Diones as Inhibitors of Human Placental Microsomol Aromatase" Mar. 1982, pp. 326-333 and p. 1-vol. 39, No. 3.

Primary Examiner—Leonard Schenkman
Assistant Examiner—Joseph A. Lipovsky
Attorney, Agent, or Firm—Bierman & Muserlian

[57] ABSTRACT

A novel steroid of the formula

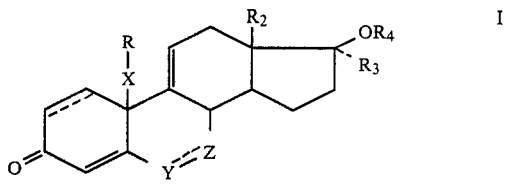

wherein X is methylene and R is an optionally substituted carbocyclic aryl or heterocyclic aryl or optionally substituted vinyl or ethynyl or X is a simple bond or —S— and R is optionally substituted carbocyclic aryl or heterocyclic aryl, $R_2$ is methyl or ethyl, $R_3$ is selected from the group consisting of optionally substituted alkyl of 1 to 8 carbon atoms and optionally substituted alkenyl and alkynyl of 2 to 8 carbon atoms, $R_4$ is selected from the group consisting of hydrogen and acyl,

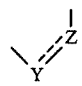

is selected from the group consisting of

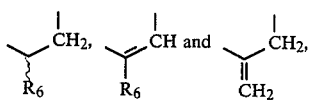

$R_6$ is selected from the group consisting of hydrogen and methyl, the wavy line indicates α or β- and the dotted line in 1(2) indicates the optional presence of a second carbon-carbon bond and novel process and intermediates therefore having anti-glucocorticoid activity.

13 Claims, No Drawings

NOVEL 10-SUBSTITUTED STEROIDS

OBJECTS OF THE INVENTION

It is an object of the invention to provide the novel 10-substituted steroids of formula I and a novel process and novel intermediates for their preparation.

It is another object of the invention to provide novel antiglucocorticoid compositions and a novel method of inducing antiglucocorticoid activity in warm-blooded animals.

These and other objects and advantages of the invention will become obvious from the following detailed description.

THE INVENTION

The novel compounds of the invention are steroids of the formula

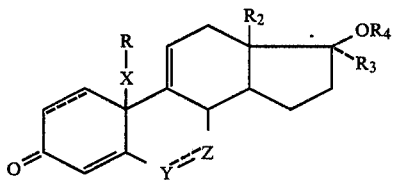

wherein X is methylene and R is an optically substituted carbocyclic aryl or heterocyclic aryl or optionally substituted vinyl or ethynyl or X is a simple bond or —S— and R is optionally substituted carbocyclic aryl or heterocyclic aryl, $R_2$ is methyl or ethyl, $R_3$ is selected from the group consisting of optionally substituted alkyl of 1 to 8 carbon atoms and optionally substituted alkenyl and alkynyl of 2 to 8 carbon atoms, $R_4$ is selected from the group consisting of hydrogen and acyl,

is selected from the group consisting of

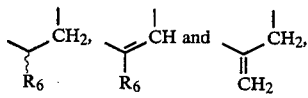

$R_6$ is selected from the group consisting of hydrogen and methyl, the wavy line indicates α or β- and the dotted line in 1(2) indicates the optional presence of a second carbon-carbon bond.

Examples of R are carbocyclic aryl such as phenyl and naphthyl; vinyl; ethynyl; and heterocyclic aryl of 5 to 6 ring atoms containing 1 to 4 heteratoms selected from the group consisting of nitrogen, sulfur and oxygen such as furyl, thienyl, pyrrolyl, oxazolyl, thiazolyl, imidazolyl, pyrazolyl, thiadiazolyl, triazolyl, oxadiazolyl, tetrazolyl, pyridinyl, pyrazinyl and pyrimidinyl.

Among the optional substituents for R group are alkyl of 1 to 4 carbon atoms such as methyl, ethyl, propyl, isopropyl, butyl, tert-butyl; alkoxy of 1 to 4 carbon atoms such as methoxy, ethoxy, propyloxy, butoxy or tert-butoxy; alkylthio of 1 to 4 carbon atoms such as methylthio, ethylthio, propylthio or butylthio; alkenyl such as vinyl or allyl; alkynyl such as ethynyl, propargyl or prop-1-ynyl; halogen such as fluorine, chlorine, bromine or iodine; haloalkyl such as trifluoromethyl, amino radicals, protected amino, monoalkylamino or dialkylamino such as methylamino or dimethylamino, optionally protected hydroxyl, mercapto, carboxyl, esterified or salified carboxyl, carbamoyl or nitro, amino, mono or dialkylaminoalkyl such as dimethylaminoethyl, carboxyalkyl such as carboxymethyl, and hydroxyalkyl such as hydroxymethyl.

The vinyl or ethynyl which R can be may be substituted by a carbocyclic or heterocyclic aryl chosen from the previous list.

The alkyl, alkenyl or alkynyl which $R_3$ can be are preferably chosen from the lists given above and $R_3$ is preferably alkynyl such as propynyl. The acyl which $R_4$ can represent is preferably a residue of a carboxylic acid of 1 to 7 carbon atoms such as acetyl, propionyl or benzoyl.

Among the preferred compounds of formula I are those of the formula

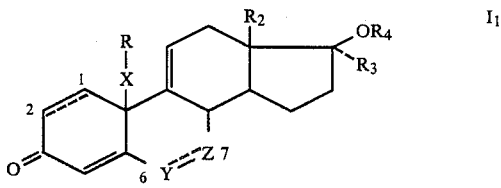

wherein X. R, $R_2$, $R_3$ and $R_4$ are defined as above,

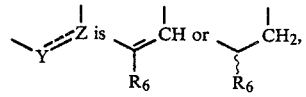

$R_6$ is hydrogen or methyl, the dotted line at position 1(2) indicates the optional presence of a second bond between the carbons, the wavy line at position 6 indicates that the substituent $R_6$ when it is a methyl radical, can be found in the α- or β-position.

Preferably, R is phenyl or phenyl substituted with a member of the group consisting of alkyl and alkoxy of 1 to 4 carbon atoms, halogen, —$NH_2$ and —N—$(AlK)_2$ and AlK is alkyl of 1 to 4 carbon atoms or pyridyl or —CH=$CH_2$ or

or ethynyl optionally substituted with a member of the group consisting of alkyl of 1 to 4 carbon atoms, phenyl, optionally esterified carboxy, hydroxymethyl and optionally protected or alkylated amino.

The protected amino may be chosen from tritylamino, or bis trimethylsilylamino and the esterified carboxy may be methoxycarbonyl, ethoxycarbonyl or tert-butoxycarbonyl. The monoalkylated or dialkylated amino is preferably methylamino or dimethylamino.

Examples of specific compounds of formula I are: 10β-benzyl-17α-(prop-1-ynyl)-$\Delta^{4,9(11)}$-estradien-17β-ol-3-one, 10β-[4-methyl-benzyl]-17α-(prop-1-ynyl)-$\Delta^{4,9(11)}$-estradien-17β-ol-3-one, 10β-(2-methylprop-2-en-1-yl)-17α-(prop-1-ynyl)-$\Delta^{4,9(11)}$-estradien-17β-ol-3-one, 10β-[(4-methoxyphenyl)-thio]-17α-(prop-1- ynyl)-$\Delta^{4,9(11)}$-estradien-17$\beta$-ol-3-one and; 10$\beta$-[2-fluoro-benzyl]-17$\alpha$-(prop-1-ynyl)-$\Delta^{4,9(11)}$-estradien-17$\beta$-ol-3-one.

The novel process of the invention for the preparation of the compounds of formula I comprises reacting a compound of the formula

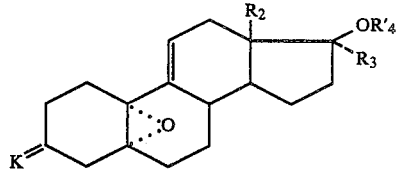

wherein $R_2$ and $R_3$ have the above significance, K is a protective group of the ketone function and $R_4'$ is hydrogen or a protective group of the hydroxyl with either a lithium compound of the formula R—X—Li, or with a magnesium compound of the formula R—X'—Mg—Hal, in which R and X have the above significances, X' is methylene or a simple bond and Hal is halogen to obtain a compound of the formula

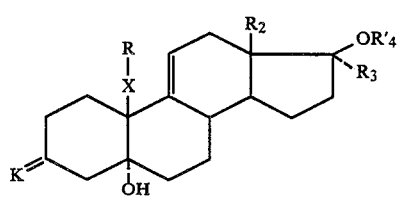

reacting the latter with an acid to obtain a compound of the formula

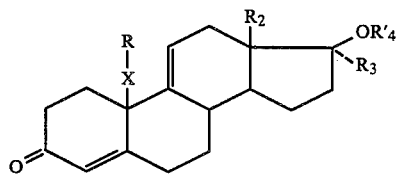

which, if necessary, is reacted with a cleavage reagent for $R_4'$ when the latter is a protective group of hydroxyl other than an acyl to obtain a compound of the formula

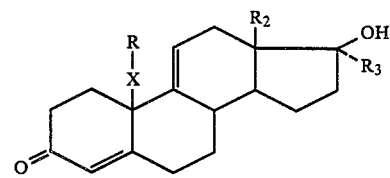

and optionally reacting a compound of formula IV with an alkyl orthoformate, then with a dehydrogenation reagent and finally, if necessary, with a cleavage reagent for $R_4'$ when the latter is a protective group of hydroxyl other than an acyl to obtain a compound of the formula

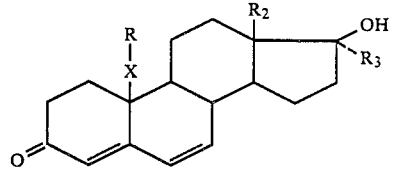

and reacting a compound of formula IV with a reagent able to introduce a methylene in position 6 to obtain a compound of the formula

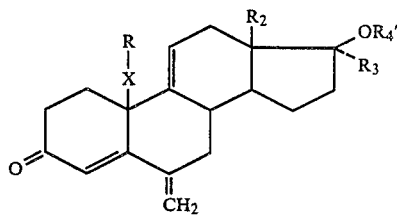

optionally reacting the latter with a cleavage reagent for $R_4'$ when the latter is a protective group of hydroxyl other than an acyl to obtain a compound of the formula

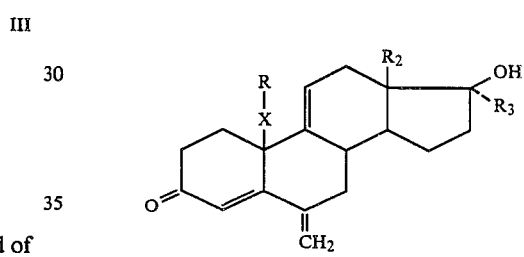

or a product of the formula V which either is reacted with a hydrogenation and possibly an epimerization reagent, then with a cleavage reagent for $R_4'$ when the latter is a protective group of hydroxyl other than an acyl to obtain a compound of the formula

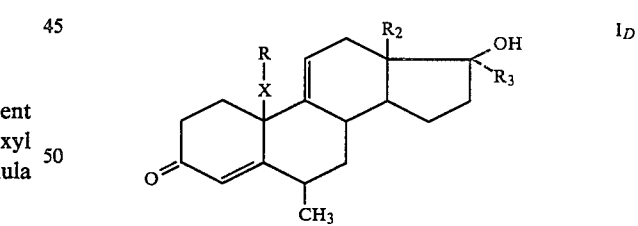

or is reacted with an isomerization agent to obtain after reaction with a cleavage reagent for $R_4'$, when the latter is a protective group of hydroxyl a compound of the formula

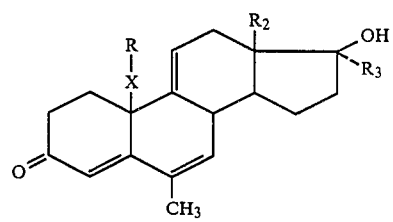

and optionally reacting the products of formulae $I_A$, $I_B$, $I_C$, $I_D$ and $I_E$ with a dehydrogenation reagent or with a microorganism able to dehydrogenate to obtain the corresponding products having unsaturation at position 1(2) and optionally reacting the products of formulae $I_A$, $I_B$, $I_C$, $I_D$ and $I_E$ and the corresponding product having unsaturation at position 1(2) with an acylation reagent.

The protective group of the ketone function is one wherein K is a ketal, thioketal, an oxime or an alkoxime and a ketal such as bismethoxy or a cyclic ketal such as ethylenedioxy is preferably used as these groups are eliminated in an acid medium. The lithium compound of the formula R—X—Li is preferably prepared in situ by the action of butyl lithium with a product of the formula R—XH and the reaction is preferably carried out at low temperature in a solvent or in a mixture of anhydrous organic solvents such as tetrahydrofuran or ethyl ether.

The reaction of the magnesium compound is carried out in the usual conditions and the magnesium compound can be prepared in situ by the action of the corresponding halide with metallic magnesium. The operation can be done with the chloride or bromide of the organomagnesium compound and the reaction is carried out in an anhydrous organic solvent such as tetrahydrofuran or ethyl ether.

The acid used to dehydrate the molecule is preferably aqueous hydrochloric acid and it can be done in a solvent miscible with water such as ethanol.

The protective group of hydroxyl at position 17 of $R_4'$ can be chosen from the known groups such as tetrahydropyrannyl or tert-butyl or an acyl such as acetyl, chloroacetyl or trifluoroacetyl. The elimination of the non-acylated groups can be carried out by known methods and is preferably done in an acid medium. The acid treatment required to transform the products of formula III into products of formula IV can moreover lead to a simultaneous elimination of $R_4'$.

The alkyl orthoformate used to convert the products of formula IV into products of formula $I_B$ is preferably ethyl orthoformate and it is done in the presence of an acid such as p-toluene sulfonic acid. Intermediate products are obtained of the formula

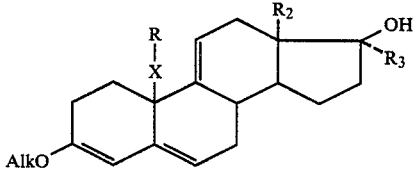

and it is on these intermediate products that a dehydrogenation reagent such as chloranile or DDQ (2,3-dichloro-5,6-dicyano benzoquinone) is reacted.

The preparation of the products of formulae V or $I_C$ starting with the product of formula IV can be carried out by the method described in Liebigs. Ann. Chem. (1983), p. 712–713 or Synthesis, (1982), p. 34–40. In a preferred mode of the process, the product of formula IV is reacted with phosphoryl chloride in the presence of formaldehyde dimethylacetal or diethylacetal and sodium acetate in a solvent such as chloroform.

The hydrogenation and the possible epimerization of the product of formula V into a product of formula $I_D$ is carried out in usual conditions and can, for example, be carried out with hydrogen in the presence of a catalyst.

The isomerization of products of formula V into products of formula $I_E$ can be carried out according to the method described in Tetrahedron Vol. 20, p. 597 (1964) or Vol. 21, p. 1619 (1965) using palladium on carbon in the presence of cyclohexane.

It can also be pointed out that the change of the products of formula IV into products of formula $I_E$ can be carried out directly without intermediate isolation of the product of formula V by the reaction of the product of formula IV with phosphoryl chloride and methoxymethyl acetate in the presence of sodium acetate in chloroform (Ann. Chem. (1983), p. 712).

The dehydrogenation reagent which is reacted with the products of formulae $I_A$, $I_B$, $I_C$, $I_D$ and $I_E$ is preferably seleninic anhydride but a derivative of benzoquinone such as chloranile or DDQ can also be used. Finally, a microorganism such as the bacterium "Arthrobacter simplex" can be used wherein the operation is done in a buffered aqueous medium. The possible acylation of the final products is carried out by the usual methods using an acyl anhydride or halide.

In a modification of the process of the invention, the compounds of formula I are prepared by reacting a compound of the formula

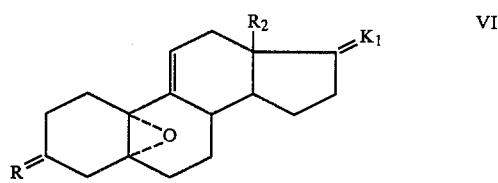

wherein $R_2$ has the above significance, K is a protective group of the ketone function and $K_1$ is a possibly protected ketone function with either with a lithium compound of the formula R—X—Li, or with a magnesium compound of the formula R—X'—Mg—Hal in which formulae R and X have the above significances, X' is methylene or a simple bond and Hal is halogen to obtain a product of the formula

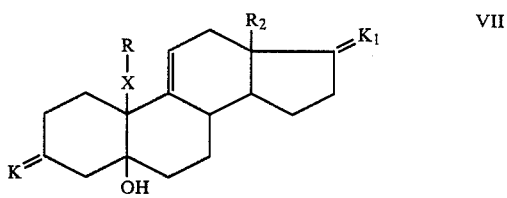

which product is reacted with either a cleavage reagent for $K_1$ when the latter is a protective group of the keto at position 17, then by a magnesium compound of the formula $R_3$—Mg—Hal$_1$ or by a lithium compound of the formula $R_3$—Li in which $R_3$ has the above significance and Hal$_1$ is halogen to obtain a product of the formula

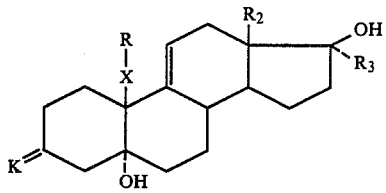

III_A which is reacted with an acid to obtain a product of formula $I_A$ as defined above and optionally subjecting the latter to a protection reaction of the hydroxyl at position 17β- and the product of formulae $I_A$ or IV thus obtained is treated by the process described above to obtain the products of formulae $I_B$, $I_C$, $I_D$ and $I_E$ and the corresponding products unsaturated at 1(2); or the product of formula VII is reacted with an acid to obtain a product of the formula

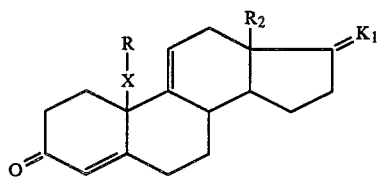

VIII which product is reacted with either an alkyl orthoformate, then with a dehydrogenation reagent to obtain a product of the formula

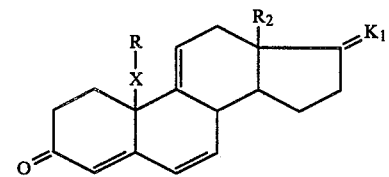

IX or with a reagent able to introduce a methylene at position 6 to obtain a product of the formula

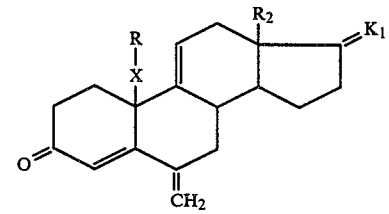

X which latter product is reacted either with a hydrogenation reagent and possibly of epimerization to obtain a product of the formula

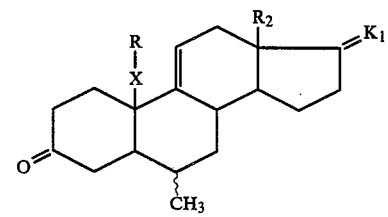

XI or with an isomerization agent to obtain a product of the formula

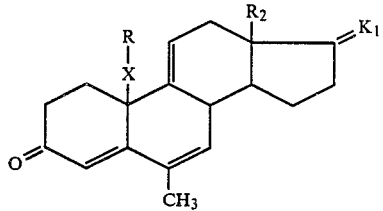

XII and the products of formulae VIII, IX, X, XI and XII are optionally reacted with a cleavage reagent for $K_1$ when the latter is a protective group of the ketone function and by a blockage agent for the ketone function at position 3, then by a magnesium compound of formula $R_3$—Mg—$Hal_1$ in which $R_3$ has the above significance and $Hal_1$ is halogen to obtain respectively, after deblocking of the ketone function at position 3, the products of formulae $I_A$, $I_B$, $I_C$, $I_D$ and $I_E$ as defined above, which can be transformed by the process described above into the corresponding products unsaturated at position 1(2) and which can be acylated.

Among the values of $K_1$ are those indicated above for K and preferably $K_1$ is

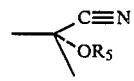

in which $R_5$ is hydrogen, trimethylsilyl or an acyl.

The reaction of the lithium compound of the formula R—X—Li or the magnesium compound of the formula R—X'—Mg—Hal with the product of formula VI is carried out under the same conditions as those described above for the action on the product of formula II.

It is the same for the other reactions carried out on the products of formulae VII and VIII. The possible protection reaction at position 17 of the product of formula $I_A$ is carried out under the usual conditions. For example, a tert-butyl halide, an acyl anhydride or dihydrofuran can be used. The possible cleavage reaction of $K_1$ which can protect the ketone function at position 17 is carried out in the usual conditions, preferably by acid hydrolysis. The possible blockage reaction of the ketone function at position 3 is also carried out in the usual conditions, preferably using one of the ketals described previously.

The novel antiglucocorticoid compositions of the invention are comprised of an antiglucocorticoidally effective amount of at least one compound of formula I and an inert pharmaceutical carrier or excipient. The compositions may be in the form of plain or sugar-coated tablets, capsules, granules, suppositories, injectable preparations, ointments, creams, gels, eye lotions prepared by the usual methods.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions of the invention are useful to combat the secondary effects of glucocorticoids as well as to combatting problems due to a hypersecretion of glucocorticoids, notably ageing in general and more particularly hypertension, glaucoma, atherosclerosis, osteoporosis, diabetes, obesity as well as immuno-depression and insomnia.

Some of the compositions of the invention also have glucocorticoid properties and are thus useful in the treatment of inflammatory reactions. They are useful for the treatment of local inflammatory reactions as for example, oedemas, dermatosis, pruritus, various forms of eczema and solar erythema or in the treatment of inflammatory manifestations of rheumatic or arthritic origin.

Among the preferred compositions of the invention are those wherein R is phenyl or phenyl substituted with a member of the group consisting of alkyl and alkoxy of 1 to 4 carbon atoms, halogen, —NH$_2$ and —N—(AlK)$_2$ and AlK is alkyl or 1 to 4 carbon atoms or pyridyl or —CH=CH$_2$ or

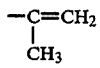

or ethynyl optionally substituted with a member of the group consisting of alkyl of 1 to 4 carbon atoms, phenyl, optionally esterified carboxy, hydroxymethyl and optionally protected or alkylated amino and specifically, the composition containing as the active ingredient one of the compounds of the group consisting of 10β-benzyl-17α-(prop-1-ynyl)-Δ$^{4,9(11)}$-estradien-17β-ol-3-one 10β-[4-methyl-benzyl]-17α-(prop-1-ynyl)-Δ$^{4,9(11)}$-estradien-17β-ol-3-one, 10β-(2-methylprop-2-en-1-yl)-17α-(prop-1-ynyl)-Δ$^{4,9(11)}$-estradien-17β-ol-3-one, 10β-[(4-methoxyphenyl)-thio]-17α-(prop-1-ynyl)-Δ$^{4,9(11)}$-estradien-17β-ol-3-one and 10β-[2-fluoro-benzyl]-17α-(prop-1-ynyl)-Δ$^{4,9(11)}$-estradien-17β-ol-3-one.

The novel method of the invention for inducing antigulcocorticoid activity in warm-blooded animals, including humans, comprises administering to warm-blooded animals an antiglucocorticoidally effective amount of at least one compound of formula I. The compounds may be administered orally, rectally or parenterally. The usual daily dose is 0.15 to 15 mg/kg depending on the condition treated, the specific compound and the method of administration.

The novel intermediate compounds of the formula

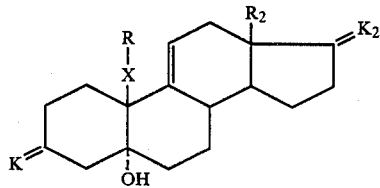

wherein X, R and R$_2$ have the above significance, K is a protective group of the ketone function and K$_2$ is either a possibly protected ketone function or

in which R$_3$ has the above significance and the hydroxyl is possibly protected are a part of the invention.

The starting products of formulae II or VI are known or can be prepared by the process described in French Pat. Nos. 2,423,486, No. 2,522,328 and European Pat. No. 0,057,115.

In the following examples there are described several preferred examples to illustrate the invention. However it should be understood that the invention is not intended to be limited to the specific embodiments.

EXAMPLE 1

10β-benzyl-17α-(prop-1-ynyl)-Δ$^{4,9(11)}$-estradien-17β-ol-3-one

STEP A: 10β-benzyl-3,3-ethylene-bisoxy-17α-(prop-1-ynyl)-Δ$^{9(11)}$-estraen-5α,17β-diol.

Over 25 minutes while maintaining the temperature between 30° and 35° C., a solution of 42.6 g of α-chlorotoluene in 220 ml of tetrahydrofuran was introduced into a mixture of 8.2 g of magnesium in 30 ml of tetrahydrofuran and the magnesium reaction was started after introduction of the first few ml of the addition of 2 ml of an ether solution of 1,2-dibromethane magnesium. The reacting mixture was allowed to return to 20° C. with stirring under nitrogen, and a solution titrating 0.5 M/l was obtained.

While maintaining the temperature at +5°/+8° C., a solution of 3.7 g of 3,3-ethylene-bisoxy-5α,10α-epoxy-17α-(prop-1-ynyl)-Δ$^{9(11)}$-estraen-17β-ol in 20 ml of tetrahydrofuran was introduced dropwise into a solution of 60 ml of magnesium benzyl chloride in tetrahydrofuran prepared as indicated above previously cooled to 0° C. The reaction mixture was stirred for 30 minutes at 0° C., then, after allowing the temperature to raise to 20° C. it was stirred for 3 hours. The mixture was poured into a mixture of 370 ml of water and ice with 37 g of ammonium chloride and after stirring for 15 minutes and decanting the aqueous phase, the residue was extracted with ethyl ether. The organic phase was washed with water, dried, concentrated to dryness under reduced pressure to obtain 8.1 g of crude product which was chromatographed over silica. Elution with a mixture of methylene chloride-acetone with 1°/$_{oo}$ of triethylamine yielded 2.435 g of 10β-benzyl-3,3-ethylene-bisoxy-17α-(prop-1-ynyl)-Δ$^{9(11)}$-estraen-5α,17β-diol followed by 1.032 g of the 10α-benzyl isomer. An analytical sample of the 10β-isomer was obtained by dissolving 440 mg in 7 ml of refluxing isopropyl ether and 2 ml of methylene chloride. The solution was filtered hot and concentrated to a small volume. After holding for 3 hours resting at 20° C., then separating and washing twice with 1 ml of isopropyl ether, the product was dried to obtain 342 mg of pure 10β-benzyl-3,3-ethylene-bisoxy-17α-(prop-1-ynyl)Δ$^{9(11)}$-estraen-5α,17β-diol melting at 200° C. and having a specific rotation of [α]$_D$=−4.45°±2° (c=0.5% in chloroform).

Analysis: C$_{30}$H$_{38}$O$_4$; molecular weight=462.635.
Calculated: %C 77.89, %H 8,28. Found: 77.9, 8.3.

STEP B: 10β-benzyl-17α-(prop-1-ynyl)-Δ$^{4,9(11)}$-estradien-17β-ol-3-one

A mixture of 2.07 g of the product of Step A, 6.2 ml of 95% ethanol and 2.07 g of sulfonic acid resin was heated at reflux for 2 hours under nitrogen and the resin was filtered and triturated with 95% ethanol. The solution was concentrated to dryness under reduced pressure to obtain 1.97 g of raw product which was chromatographed over silica (eluent: methylene chloride-acetone 9-1) to obtain 1.24 g of 10β-benzyl-17α-(prop-1-ynyl)-Δ$^{9(11)}$-estraen-5α,17β-diol-3-one.

A solution of 1.08 g of said product in 10.8 ml of ethanol was heated to 40° C. and then 5.40 ml of 2N hydrochloric acid are added in a single lot. The mixture was heated to 60° C. under nitrogen while stirring for 6 hours 30 minutes and was then cooled to 20° C. and 15 ml of a saturated aqueous solution of sodium bicarbonate was added. Then 15 ml of methylene chloride were added and the aqueous phase was decanted. The residue was extracted with methylene chloride and the organic phase was washed with water, dried, concentrated to dryness under reduced pressure to obtain 1.04 g of raw product which was chromatographed over silica (eluent: methylene chlorideacetone 95-5) to obtain 932 mg of 10$\beta$-benzyl-17$\alpha$-(prop-1-ynyl)-$\Delta^{4,9(11)}$-estradien-17$\beta$-ol-3-one. The product was crystallized by dissolving at reflux in a mixture of 7 ml of isopropyl ether and 8 ml of methylene chloride and then was filtered hot. The filtrate was concentrated to a reduced volume and after standing at 3 hours at 20° C., separating and washing with 0.7 ml of isopropyl ether, 902 mg of the desired product was obtained melting at 217° C. and having a specific rotation of $[\alpha]_D = +16.5° \pm 2°$ C. (c=0.7% in chloroform).

U.V. Spectrum (ethanol): infl. 215 nm $E_1^1 = 365$; max. 244 nm $E_1^1 = 332$, $\epsilon = 13300$; infl. 311 nm $E_1^1 = 2$.

EXAMPLE 2

10$\beta$-[(2-methyl-benzyl)]-17$\alpha$-(prop-1-ynyl)-$\Delta^{4,9(11)}$-estradien-17$\beta$-ol-3-one STEP A: 3,3-bismethoxy-10$\beta$-[(2-methyl-benzyl)]-17$\alpha$-(prop-1-ynyl)-$\Delta^{9(11)}$-estraen-5$\alpha$,17$\beta$-diol 20 ml of ethyl ether and 0.2 ml of $\alpha$-chloro-orthoxylene were added under nitrogen with stirring to 5.5 g of magnesium turnings and then over an hour, a solution of 32 ml of $\alpha$-chloro-orthoxylene in 250 ml of ether was added dropwise so as to maintain the temperature at 35° C. After stirring for an hour, a solution of 0.5 M/l of $\alpha$-chloro-orthoxylene magnesium was obtained.

A solution of 30 ml of tetrahydrofuran and 10 g of product comprising 50% of 3,3-bismethoxy-5$\alpha$,10$\alpha$-epoxy-17$\alpha$-(prop-1-ynyl)-$\Delta^{9(11)}$-estraen-17$\beta$-ol, 30% of 3,3-bismethoxy-5$\alpha$,10$\alpha$-epoxy-17$\alpha$-(prop-1-ynyl)-$\Delta^{9(11)}$-estraen-17$\beta$-ol and 20% 3,3-bismethoxy-17$\alpha$-(prop-1-ynyl)-$\Delta^{5(10),9(11)}$-estradien-17$\beta$-ol was added over 20 minutes to 215 ml of magnesium prepared as above while maintaining the temperature at 20° C. The mixture was stirred for 2 hours and was poured with stirring into a solution of 100 g of ammonium chloride in 1 liter of water. After stirring vigorously for 15 minutes and decanting, the aqueous phase was extracted with ether. The combined organic phases were washed with water, dried, filtered and concentrated to dryness under reduced pressure (eluent: methylene chloride-acetone 95-5, triethylamine 1%) to obtain 2.3 g of 3,3-bismethoxy-10$\beta$-[(2-methylbenzyl)]-17$\alpha$-(prop-1-ynyl)-$\Delta^{9(11)}$-estraen-5$\alpha$,17$\beta$-diol with an Rf=0.5.

Analysis: $C_{31}H_{42}O_4$; molecular weight=478.68. Calculated: %C 77.78, %H 8.84. Found: 77.7, 9.1.

STEP B: 10$\beta$-[(2-methyl-benzyl)]-17$\alpha$-(prop-1-ynyl)-$\Delta^{4,9(11)}$-estradien-17$\beta$-ol-3-one A solution of 2.5 g of the product of Step A in 25 ml of 96% ethanol was heated to 40° C. and 9.6 ml of 2N hydrochloric acid were added all at once. After refluxing for 45 minutes, the product crystallized and after cooling to ambient temperature, filtering the product and washing it with isopropyl ether, 1.6 g of product were obtained which was dissolved in a heated mixture of 20 ml of isopropyl ether and 15 ml of methylene chloride. The impurities were filtered off and the filtrate was left to crystallized at ambient temperature. After filtering, washing and drying, 1.4 g of 10$\beta$-[(2-methyl-benzyl)]-17$\alpha$-(prop-1-ynyl)-$\Delta^{4,9(11)}$-estradien-17$\beta$-ol-3-one melting at 220° C. with an Rf=0.5 (methylene chloride: 95, acetone: 5) were obtained.

Analysis: $C_{29}H_{34}O_2$; molecular weight=414.56. Calculated: %C 84.02, %H 8.26. Found: 84.2, 8.4.

EXAMPLE 3

10$\beta$-[2-chlorobenzyl]-17$\alpha$-(prop-1-ynyl)-$\Delta^{4,9(11)}$-estradien-17$\beta$-ol-3-one STEP A: 3,3-bismethoxy-10$\beta$-[2-chloro-benzyl]-17$\alpha$-(prop-1-ynyl)-$\Delta^{9(11)}$-estraen-5$\alpha$,17$\beta$-diol The reaction was started by adding 0.2 ml of 1,2-dibromoethane to a mixture of 2.05 g of magnesium turnings, 7 ml of ether and 0.2 ml of o-chlorobenzyl chloride and then, over 45 minutes and without going above 33°–35° C., a solution of 10.5 g of o-chlorobenzyl chloride in 61 ml of ether was added dropwise to obtain a solution titrating 0.9 M/l of magnesium orthochloro benzyl chloride.

54 ml of magnesium compound prepared as above were cooled to 0° C. and over 25 minutes, a solution of 6.05 g of 3,3-bismethoxy-5$\alpha$,10$\alpha$-epoxy-17$\alpha$-(prop-1-ynyl)-$\Delta^{9(11)}$-estra-en-17$\beta$-ol containing 5$\beta$,10$\beta$-epoxide in 33 ml of tetrahydrofuran was added. The mixture stood for an hour at 0°/5° C. and then was brought to ambient temperature. After pouring into 400 ml of iced water containing 40 g of ammonium chloride, agitating for 15 minutes, decanting, extracting with ether, washing with water, drying, separating and then bringing to dryness, 12 g of product were obtained which was purified by chromatography over silica. Elution with a mixture of methylene chloride-acetone (95:5) yielded 3.4 g of 3,3-bismethoxy-10$\beta$-[2-chloro-benzyl]-17$\alpha$-(prop-1-ynyl)-$\Delta^{9(11)}$-estraen-5$\alpha$,17$\beta$-diol with an Rf=0.55.

STEP B: 10$\beta$-[2-chloro-benzyl]-17$\alpha$-(prop-1-ynyl)-$\Delta^{4,9(11)}$-estradien-17$\beta$-ol-3-one A solution of 2.7 g of the product of Step A in 27 ml of 96% ethanol was heated to 40° C. and 10.8 ml of 2N hydrochloric acid were added all at once. The mixture was refluxed for 45 minutes and then was cooled to ambient temperature. The crystallized product was filtered, washed with a mixture of 30 ml of ethanol and 10 ml of water. After drying, 1.8 g of 10$\beta$-[2-chloro-benzyl]-17$\alpha$-(prop-1-ynyl)-$\Delta^{4,9(11)}$-estradien-17$\beta$-ol-3-one were obtained which was dissolved by heating in a mixture of 40 ml of isopropyl ether and 20 ml of methylene chloride, was separated hot, then allowed to crystallize at ambient temperature for 3 hours. After filtering, washing with isopropyl ether and drying, 1.65 g of the said product melting at 201° C. and having a specific rotation of $[\alpha]_D = +36° \pm 2°$ (c=0.6% in chloroform) were obtained.

U.V. Spectrum (ethanol): infl. 218 nm $E_1^1 = 402$, $\epsilon = 18800$; max. 243 nm $E_1^1 = 302$, $\epsilon = 14100$; infl. 275 nm $E_1^1 = 40$.

EXAMPLE 4

10$\beta$-[4-methyl-benzyl]-17$\alpha$-(prop-1-ynyl)-$\Delta^{4,9(11)}$-estradiene-17$\beta$-ol-3-one STEP A: 3,3-bismethoxy-10$\beta$-[4-methyl-benzyl]-17$\alpha$-(prop-1-ynyl)-$\Delta^{9(11)}$-estraen-5$\alpha$,17$\beta$-diol The reaction was started by adding 0.2 ml of 1,2-dibromoethane to a mixture of 4.1 g of magnesium turnings, 14 ml of ether and 0.2 ml of p-methylbenzyl chloride. The temperature rose to 30°–35° C. and then over an hour, a solution of 23 ml of p-methylbenzyl chloride in 180 ml of ether was added dropwise. The mixture then stood for 1 hour with stirring at ambient temperature and a solution titrating 0.5 M/1 of magnesium p-methylbenzyl chloride was obtained.

Then, over 20–25 minutes, a solution of 10 g of 3,3-bismethoxy-5α,10α-epoxy-17α-(prop-1-ynyl)-Δ$^{9(11)}$-estraen-17β-ol containing 5β,10β-epoxide in 50 ml of tetrahydrofuran was added dropwise to 215 ml of the magnesium compound prepared above. The mixture was stirred for an hour and half at ambient temperature and then was poured into a liter of water containing 100 g of ammonium chloride. After stirring for 15 minutes, the organic phase was decanted, and extracted with ether.

The organic phases were washed with water, dried, filtered and then evaporated to dryness under reduced pressure to obtain 25 g of crude product which was chromatographed over silica. Elution with methylene chloride-acetone mixture (95-5) with 1% triethylamine yielded 5.4 g of 3,3-bismethoxy-10β-[4-methyl-benzyl]-17α-(prop-1-ynyl)-Δ$^{9(11)}$-estraen-5α,17β-diol with an Rf=0.4 and melting at 170° C.

Analysis: $C_{31}H_{42}O_4$; molecular weight=478.68. Calculated: %C 77.78, %H 8.84. Found: 77.9, 8.9.

STEP B: 10β-[4-methyl-benzyl]-17α-(prop-1-ynyl)-Δ$^{4,9(11)}$-estradien-17β-ol-3-one A solution of 4.6 g of the product of Step A in 46 ml of 96°/$_{oo}$ ethanol was heated to 40° C., then 19 ml of 2N hydrochloric acid were added in a single lot. The mixture was refluxed for 45 minutes and then was cooled to ambient temperature. The crystallized product was filtered and washed with the minimum of an ethanol-water mixture (45:20). After drying under reduced pressure, 3 g of product were obtained which was purified by recrystallization hot from 100 ml of an isopropyl ether-methylene chloride mixture (1-1). After filtering off impurities, concentrating to three quarters volume and standing to crystallize at ambient temperature for 3 hours, 2.6 g of 10β-[4-methyl-benzyl]-17α-(prop-1-ynyl)-Δ$^{4,9(11)}$-estradien-17β-ol-3-one melting at 220° C. and with an Rf=0.5 (methylene chloride-acetone (95:5) triethylamine 1°/$_{oo}$) and a specific rotuation of $[\alpha]_D$=+18°±1°=(c=1% in chloroform) were obtained.

U.V. Spectrum (ethanol): max. 222 nm $E_1^1$=425, $\epsilon$=17600; max. 240 nm $E_1^1$=302, $\epsilon$=12500.

EXAMPLE 5

10β-(2-propenyl)-17α-(prop-1-ynyl)-Δ$^{4,9(11)}$-estradien-17β-ol-3-one

STEP A: 3,3-bismethoxy-10β-(2-propenyl)-17α-(prop-1-ynyl)-Δ$^{9(11)}$-estraen-5α,17β-diol To a mixture of 8.51 g of magnesium turning and 85 ml of ethyl ether, several ml of a solution of 31.4 ml of allyl chloride in 170 ml of ethyl ether were added and when the reaction started, the rest of the solution was added over 45 minutes at +5° C. The mixture was stirred for 90 minutes at 20° C. and a solution titrating 0.9 M/1 of magnesium allyl chloride was obtained.

A solution of 10 g of product comprising two-thirds of 3,3-bismethoxy-5α,10α-epoxy-17α-(prop-1-ynyl)-Δ$^{9(11)}$-estraen-17β-ol and one-third of 5β,10β-epoxide was added dropwise over 30 minutes to 118 ml of the above magnesium compound solution. After stirring for 1 hour at 20° C., and standing for 16 hours at 20° C., the reaction mixture was poured into an aqueous solution of ammonium chloride and was extracted with ethyl ether.

The organic phase was washed with a saturated aqueous solution of sodium chloride, dried and concentrated to dryness under reduced pressure. The residue was purified by chromatography over silica and elution with a methylene chloride and acetone mixture (95-5) with 1°/$_{oo}$ triethylamine to obtain 5.5 g of 3,3-bismethoxy-10β-(2-propenyl)-17α-(prop-1-ynyl)-Δ$^{9(11)}$-estraen-5α,17β-diol with an Rf=0.45.

STEP B: 10β-(2-propenyl)-17α-(prop-1-ynyl)-Δ$^{4,9(11)}$-estradien-17β-ol-3-one 26.4 ml of 2N hydrochloric acid were added to a solution of 5.5 g of 3,3-bismethoxy-10β-(2-propenyl)-17α-(prop-1-ynyl)-Δ$^{9(11)}$-estraen-5α,17β-diol of Step A in 55 ml of ethanol and the mixture was stirred for 45 minutes in a nitrogen atmosphere and cooled to +5° C. The pH was adjusted to 7 by addition of a 2N aqueous sodium hydroxide solution and after extracting with methylene chloride, the organic phase was washed with water, dried, and concentrated to dryness under reduced pressure. The residue was purified by chromatography over silica and elution with a methylene chloride and acetone mixture (95/5) yielded 3 g of crude product which was purified by triturating, then crystallizing from isopropyl ether to obtain 2.756 g of the said product melting at 138° C. and having a specific rotation of $[\alpha]_D$=+20.5°±1.5 (c=0.8% in ethanol).

U.V. Spectrum (ethanol): max. 242–243 nm $E_1^1$=429, $\epsilon$=15000.

EXAMPLE 6

10β-[4-fluorobenzyl]-17α-(prop-1-ynyl)-Δ$^{4,9(11)}$-estradien-17β-ol-3-one

STEP A: 3,3-bismethoxy-10β-[4-fluorobenzyl]-17α-(prop-1-ynyl)-Δ$^{9(11)}$-estraen-5α,17β-diol A solution of 23.8 ml of 4-fluorochlorotoluene in 115 ml of ethyl ether was added dropwise over 3 hours and 15 minutes to 8.51 g of magnesium turnings in 85 ml of ethyl ether and while keeping the temperature below 33° C., stirring was continued for a further 2 hours. The temperature returned to 20° C. and a solution titrating 1.1 M/1 of magnesium 4-fluorochlorotoluene was obtained.

A solution of 10 g of product comprising two-thirds of 3,3-bismethoxy-5α,10α-epoxy-17α-(prop-1-ynyl)-Δ$^{9(11)}$-estraen-17β-ol and one-third of 5β,10β-epoxide in 50 ml of tetrahydrofuran was added over 15 minutes at 13° C. to 98 ml of the above solution of magnesium compound. After stirring for 15 hours at 20° C., the reaction mixture was poured into an aqueous ammonium chloride solution and was extracted with ethyl ether. The organic phase was concentrated to dryness by distillation under reduced pressure and the residue was chromatographed over silica. Elution with a methylene chloride, acetone and triethylamine mixture (95/5/0.1) yielded 5.9 g of 3,3-bismethoxy-10β-[4-fluorobenzyl]-17α-(prop-1-ynyl)-Δ$^{9(11)}$-estraen-5α,17β-diol with an Rf=0.4.

STEP B: 10β-[4-fluorobenzyl]-17α-(prop-1-ynyl)-Δ$^{4,9(11)}$-estradien-17β-ol-3-one 24.4 ml of a 2N aqueous hydrochloric acid solution were added to a solution of 5.9 g of the product of Step A in 59 ml of ethanol, and the mixture was refluxed with stirring for 75 minutes and then was cooled to 15° C. The pH was brought to 7 with a 2N aqueous solution of sodium hydroxide, after which extraction with methylene chloride was effected. The extracts were washed with water, dried and concentrated to dryness under reduced pressure. The residue was chromatographed over silica and eluted with a methylene chloride and acetone mixture (95/5). The product was crystallized twice from ethanol to obtain 2.165 g of 3,3-bismethoxy-10β-[4-fluorobenzyl]-17α-(prop-1-ynyl)-Δ$^{9(11)}$-estraen-5α, 17β-diol melting at 240° C. and having a specific rotation of [α]$_D$=+8°±2° (c=0.5% in ethanol). P0 U.V. Spectrum: max. 244 nm $E_1^1$=341, ε=14300; infl. 270 nm $E_1^1$=89.

EXAMPLE 7

10β-(2-methyl-prop-2-en-1-yl)-17α-(prop-1-ynyl)-Δ$^{4,9(11)}$-estradien 17β-ol-3-one STEP A: 3,3-bismethoxy-10β-(2-methyl-prop-2-en-1-yl)-17α-(prop-1-ynyl)-Δ$^{9(11)}$-estraen-5α,17β-diol Over 4 hours 15 minutes at +10° C., 26.8 ml of 2-chloropropene were added to 38.9 g of magnesium turnings in 200 ml of tetrahydrofuran. After stirring for 2 hours, and letting the temperature rise to +20° C., a solution titrating 0.5M/l magnesium 1-chloro-2-methyl-prop-2-ene was obtained.

Over 15 minutes under nitrogen with stirring, a solution of 10 g of product comprising two-thirds of 3,3-bismethoxy-5α,10α-epoxy-17α-(prop-1-ynyl)-Δ$^{9(11)}$-estraen-17β-ol and one-third of 5β,10β-epoxide in 50 ml of tetrahydrofuran was added dropwise to 214 ml of the above magnesium solution. The temperature was allowed to return to 20° C. and stirring was continued for 20 hours. The reaction mixture was poured into an aqueous ammonium chloride solution and then was extracted with ethyl ether. The extracts were washed with a saturated aqueous sodium chloride solution and concentrated to dryness under reduced pressure. The residue was chromatographed over silica and eluted with a mixture of methylene chloride, acetone and triethylamine (95-5-0.1) to obtain 5.5 g of 3,3-bismethoxy-10β-(2-methyl-prop-2-en-1-yl)-17α-(prop-1-ynyl)-Δ$^{9(11)}$-estraen-5α,17β-diol with an Rf=0.4.

STEP B: 10β-(2-methyl-prop-2-en-1-yl)-17α-(prop-1-ynyl)-Δ$^{4,9(11)}$-estradien-17β-ol-3-one 25 ml of a 2N aqueous hydrochloric acid solution were added with stirring under nitrogen to a solution of 5.4 g of the product of Step A in 54 ml of ethanol and stirring was continued for 45 minutes at reflux. After cooling to +5° C. and adjusting the pH to 7 by addition of a 2N aqueous solution of sodium hydroxide, extraction was effected with methylene chloride. The methylene chloride phase was washed with water, dried and concentrated to dryness under reduced pressure. The residue was chromatographed over silica and eluted with a methylene chloride and acetone mixture (95-5). The product was twice crystallized from isopropyl ether to obtain 1.92 g of 10β-(2-methyl-prop-2-en-1-yl)-17α-(prop-1-ynyl)-Δ$^{4,9(11)}$-estradien 17β-ol-3-one with an Rf=0.35 and melting at 133° C. and having a specific rotation of [α]$_D$=−19°±2° (c=0.5% in ethanol).

Analysis: $C_{25}H_{32}O_2$; molecular weight=364.51. Calculated: %C 82.37, %H 8.85. Found: 82.1, 9.0.

EXAMPLE 8

10β-(prop-2-ynyl)-17α-(prop-1-ynyl)-Δ$^{4,9(11)}$-estradien-17β-ol-3-one

STEP A: 3,3-bismethoxy-10β-(prop-2-ynyl)-17α-(prop-1-ynyl)-Δ$^{9(11)}$-estraen-5α,17β-diol Using the procedure of the previous examples, a solution titrating 1.55M/l magnesium 1-bromoprop-2-yne was obtained.

A solution of 10 g of product comprising two-thirds of 3,3-bismethoxy-5α,10α-epoxy-17α-(prop-1-ynyl)-Δ$^{9(11)}$-estraen-17β-ol and one-third of 5β,17β-epoxide in 50 ml of tetrahydrofuran was added with stirring under nitrogen over 20 minutes to 69 ml of the above solution of magnesium compound. Stirring was continued for 2 hours and 40 minutes while letting the temperature return to 20° C. and then, after pouring with agitation into an aqueous solution of ammonium chloride. The mixture was extracted with ethyl ether and the organic phase was washed with water saturated with sodium chloride, dried and concentrated to dryness under reduced pressure. The residue was chromatographed over silica and eluted with a methylene chloride, acetone and triethylamine mixture (95-5-0.1) to obtain 3.3 g of 3,3-bismethoxy-10β-(prop-2-ynyl)-17α-(prop-1-ynyl)-Δ$^{9(11)}$-estraen-5α,17β-diol with an Rf=0.4 and melting at 217° C.

STEP B: 10β-(prop-2-ynyl)-17α-(prop-1-ynyl)-Δ$^{4,9(11)}$-estradien-17β-ol-3-one 13.5 ml of a 2N aqueous hydrochloric acid solution were added with stirring under nitrogen to a suspension of 2.8 g of the product of Step A in 28 ml of ethanol and the mixture was refluxed with stirring for 45 minutes and was then cooled to +5° C. The pH was adjusted to 7 by addition of a 2N aqueous sodium hydroxide soluton and was extracted with methylene chloride. The organic phase was washed with water and concentrated to dryness under reduced pressure. The residue was chromatographed over silica and eluted with a methylene chloride and acetone mixture (95/5). After twice crystallizing from ispropyl ether, 1.336 g of 10β-(prop-2-ynyl)-17α-(prop-1-ynyl)-Δ$^{4,9(11)}$-estradien-17β-ol-3-one melting at 163° C. with an Rf=0.37 and a specific rotation of [α]$_D$=−32°±2° (c=0.6% in ethanol) were obtained.

U.V. Spectrum (ethanol): max. 240 nm $E_1^1$=467, ε=16300.

EXAMPLE 9

10β-[(2-pyridinyl)-thiol]-17α-(prop-1-ynyl)-Δ$^{4,9(11)}$-estradien-17β-ol-3-one STEP A: 3,3-bismethoxy-10β-[(2-pyridinyl)-thio]-17α-(prop-1-ynyl)-Δ$^{9(11)}$-estraen-5α,17β-diol 87.5 ml of a 1.6N solution of butyllithium in hexane were added with stirring under nitrogen over 30 minutes to a solution of 17.78 g of 2-mercapto pyridine in 75 ml of tetrahydrofuran at −35° C. After stirring for an hour while letting the temperature return to 0° C., a suspension of the lithium derivative of the formula

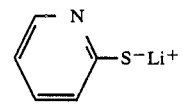

was obtained.

Over 20 minutes at 0° C., a solution of 12 g of product comprising two-thirds of 3,3-bismethoxy-5α,10α-epoxy-17α-(prop-1-ynyl)-Δ$^{9(11)}$-estraen-17β-ol and one-third of 5β,10β-epoxide in 60 ml of tetrahydrofuran was added to the said suspension of lithium derivative and after stirring for 2 hours and 30 minutes while allowing the temperature to return to 20° C., the reaction mixture was introduced into an aqueous solution of ammonium chloride and extracted with methylene chloride. The extracts were washed with water, dried and concentrated to dryness under reduced pressure. The residue was chromatographed over silica and eluted with a cyclohexane-ethyl acetate mixture (1-1) to obtain 9.6 g of 3,3-bismethoxy-10β-[(2-pyridinyl)-thio]-17α-(prop-1-ynyl)-Δ$^{9(11)}$-estraen-5α,17β-diol with an Rf=0.37 (product I).

IR Spectrum (chloroform): Absorption at 3420 cm$^{-1}$ attributed to 5-hydroxy; Absorption at 1573, 1560 cm$^{-1}$ of the conjugated system; Absorption at 3603, 2240 cm$^{-1}$ attributed to

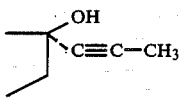

In the chromatography, moreover, 1.1 g of 3,3-bismethoxy-10α-[(2-pyridinyl)-thio]-17α-(prop-1-ynyl)-Δ$^{9(11)}$-estraen-5β,17β-diol with an Rf=0.27 (product II) were isolated.

IR Spectrum (chloroform): Absorption at 3440 cm$^{-1}$ attributed to 5-hydroxy.

STEP B: 10β-[(2-pyridinyl)-thio]-17α-(prop-1-ynyl)-Δ$^{4,9(11)}$-estradien-17β-ol-3-one 30 ml of a 2N aqueous hydrochloric acid solution were added to a solution of 7.5 g of the product I of Step A in 150 ml of ethanol. The mixture was stirred for 20 hours at 40° C. and then the pH was adjusted to 7 by addition of a saturated aqueous solution of sodium bicarbonate. After extracting with ethyl acetate, washing with water, drying and concentrating to dryness under reduced pressure, the residue was chromatographed over silica and eluted with a methylene chloride-acetone mixture (9/1). After triturating with ethyl ether and crystallizing from ethanol, 0.966 g of 10β-[(2-pyridinyl)-thio]-17α-(prop-1-ynyl)-Δ$^{4,9(11)}$-estradien-17β-ol-3-one melting at 192° C. and with an Rf=0.35 and having a specific rotation of $[\alpha]_D=+174.5°$ (c=0.4% in ethanol) were obtained.

Analysis: $C_{26}H_{29}NO_2S$; molecular weight=419.50. Calculated: %C 74.42, %H 6.96, %N 3.33, %S 7.64. Found: 74.2, 7.0, 3.3, 7.5.

During chromatography, moreover, 0.6 g of 17α-(1-propynyl)-Δ$^{1,3,5(10),9(11)}$-estratetraen-3,17β-diol with an Rf=0.55 was isolated.

IR Spectrum (chloroform): Absorption at 3600 cm$^{-1}$ attributes to OH; Absorption at 2130 cm$^{-1}$ at c≡c; Absorption at 1630 cm$^{-1}$ attributed to Δ9(11).

EXAMPLE 10

10β-[(4-methoxyphenyl)-thio]-17α-(prop-1-ynyl)-Δ$^{4,9(11)}$-estradien-17β-ol-3-one STEP A: 3,3-bismethoxy-10β-[(4-methoxyphenyl)-thio]-17α-(prop-1-ynyl)-Δ$^{9(11)}$-estraen-5α,17β-diol 73 ml of a 1.6M/l solution of butyllithium in hexane were added under nitrogen with stirring to a solution of 18.8 g of p-methoxy benzene thiol in 75 ml of tetrahydrofuran over 30 minutes at −35° C. After stirring while allowing the temperature to return to 0° C., a solution of the lithium derivative of the formula

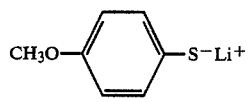

was obtained.

Over 30 minutes at 0° C., 12 g of a solution of product comprising two-thirds of 3,3-bismethoxy-5α,10α-epoxy-17α-(prop-1-ynyl)-Δ$^{9(11)}$-estraen-17β-ol and one-third of 5β,10β-epoxide in 60 ml of tetrahydrofran were added to the said solution of lithium derivative and after stirring for 2 hours and 10 minutes while allowing the temperature to return to 20° C., the reaction mixture was introduced into an aqueous solution of ammonium chloride. The mixture was extracted with ethyl ether and the extracts were washed with water and concentrated to dryness under reduced pressure. The residue was chromatographed over silica and eluted with a methylene chloride-acetone mixture (95/5) to obtain 10.2 g of 3,3-bismethoxy-10β-[(4-methoxyphenyl)-thio]-17α-(prop-1-ynyl)-Δ$^{9(11)}$-estraen-5α,17β-diol with an Rf=0.4 (product I).

In the chromatography, moreover, 3.7 g of 3,3-bismethoxy-10β-[(4-methoxyphenyl)-thio]-17α-(prop-1-ynyl)-Δ$^{9(11)}$-estraen-5β,17β-diol with an Rf=0.3 (product II) were isolated.

STEP B: 10β-[(4-methoxyphenyl)-thio]-17α-(prop-1-ynyl)-Δ$^{4,9(11)}$-estradien-17β-ol-3-one 5.5 g of product of Step A were introduced under nitrogen with stirring into 110 ml of ethanol and 22 ml of a 2N aqueous hydrochloric acid solution were added with stirring for 20 hours at 40° C. After cooling to +5° C., the pH was adjusted to 7 by the addition of a saturated aqueous solution of sodium bicarbonate. After extracting with methylene chloride, the extracts were washed with water, dried, and concentrated to dryness under reduced pressure. The residue was chromatographed over silica and eluted with a methylene chloride-acetone mixture (95/5), followed by triturating with ethyl ether, crystallizing from a mixture of 15 ml of ethanol and 10 ml of methylene chloride, and eliminating the methylene chloride by distillation. Then, after cooling, separating and drying under reduced pressure, 2.290 g of 10β-[(4-methoxyphenyl)-thio]-17α-(prop-1-ynyl)Δ-$^{4,9(11)}$-estradien-17β-ol-3-one with a melting point of 206° C. and a Rf=0.27 and a specific rotation of $[\alpha]=+93°$ (c=0.6% in ethanol) were obtained.

U.V. Spectrum (ethanol): max. 234 nm $E_1^1=532$, $\epsilon=23900$; infl. 245 nm $E_1^1=333$, $\epsilon=14900$; infl. 282 nm $E_1^1=160$, $\epsilon=7200$.

EXAMPLE 11

10β-[4-methyl-benzyl]-17α-(1-prop-1-ynyl)-Δ$^{1,4,9(11)}$-estratrien-17β-ol-3-one 1.56 g of seleninic phenyl anhydride were added to a solution of 1.21 g of 10β-[4-methyl-benzyl]-17α-(prop-1-ynyl)-Δ$^{4,9(11)}$-estradiene-17β-ol-3-one obtained at Step B of Example 4 in 24 ml of tetrahydrofuran, and the mixture was refluxed with stirring for 22 hours. After cooling, the reaction mixture was introduced at +5° C. into a saturated aqueous sodium bicarbonate solution and the precipitate formed was separated to obtain 0.354 g of 10β-[4-methylbenzyl]-17α-(1-prop-1-ynyl)-Δ$^{1,4,9(11)}$-estratrien-17β-ol-3-one melting at 262° C. The mother liquors were extracted with ethyl acetate and the extracts were concentrated to dryness. The residue was chromatographed over silica and eluted with a methylene chloride-acetone mixture (95/5) to obtain 0.723 g of expected product melting at +262° C. The two fractions of the product were combined (1.077 g) and crystallized twice from a mixture of ethanol and methylene chloride to obtain 0.848 g of pure product melting at 262° C. and having a Rf=0.34 and a specific rotation of $[\alpha]_D = -60° \pm 2.50°$ C. (c=0.5% in chloroform).

U.V. Spectrum (ethanol): max. 222 nm $E_1^1=476$, $\epsilon=19600$; max. 241 nm $E_1^1=330$, $\epsilon=13600$; infl. 265 nm $E_1^1=170$, $\epsilon=7000$.

EXAMPLE 12

10β-[2-fluorobenzyl]-17α-(prop-1-ynyl)-Δ$^{4,9(11)}$-estradien-17β-ol-3-one

STEP A: 3,3-bismethoxy-10β-[2-fluorobenzyl]-17α-(prop-1-ynyl)-Δ$^{9(11)}$-estraen-5α,17β-diol 0.5 ml of 2-fluorobenzyl chloride were added with stirring to a mixture of 8.2 g of magnesium turnings in 30 ml of ethyl ether and after the reaction started, a solution of 40 ml of 2-fluorobenzyl chloride in 220 ml of ethyl ether was added dropwise over about 1 hour while keeping the temperature below 35° C. and then the temperature was allowed to return to 20° C. over 30 minutes to obtain a solution of magnesium compound titrating 1.25M/l of magnesium 2-fluorobenzyl chloride.

At 0° C., a solution of 10 g of product composed of 50% of 3,3-bismethoxy-5α,10α-epoxy-17α-(prop-1-ynyl)-Δ$^{9(11)}$-estraen-17β-ol, 30% of 5β,10β-epoxide and 20% of 3,3-bismethoxy-17α-(prop-1-ynyl)-Δ$^{9(11)}$-estradien-17-ol in 50 ml of tetrahydrofuran was added with stirring dropwise over about 25 minutes to 90 ml of the above solution of the magnesium compound for 30 minutes at 0° C. After allowing the temperature to return to ambient over 90 minutes, the reaction mixture was introduced into an aqueous ammonium chloride solution and was extracted with ethyl ether. The extracts were washed with water and concentrated to dryness by distillation under reduced pressure. The residue was chromatographed over silica and eluted with a methylene chloride, acetone and triethylamine mixture (95/5/0.1) to obtain 2.75 g of 3,3-bismethoxy-10β-[2-fluorobenzyl]-17α-(prop-1-ynyl)-Δ$^{9(11)}$-estraen-5α,17β-diol (product I) with an Rf=0.55.

U.V. Spectrum (ethanol): max. 244 nm $E_1^1=12$; max. 257 nm $E_1^1=18$; max. 263 nm $E_1^1=24$; max. 263 nm $E_1^1=25$.

In the chromatography, moreover, 1.45 g of 3,3-bismethoxy-10α-[2-fluorobenzyl]-17α-(prop-1-ynyl)-Δ$^{9(11)}$-estraen-5α,17β-diol (product II) with an Rf=0.40 were obtained. In the chromatography, a third fraction composed of 3,3-bismethoxy-10β-[2-fluorobenzyl]-17α-(prop-1-ynyl)-Δ$^{9(11)}$-estraen-5α,17β-diol (product III) with an Rf=0.45 were obtained.

STEP B: 10β-[2-fluorobenzyl]-17α-(prop-1-ynyl)-Δ$^{4,9(11)}$-estradien-17β-ol-3-one At 40° C., 10.8 ml of a 2N aqueous solution of hydrochloric acid were introduced into a solution of 2.6 g of product (I) of Step A in 26 ml of ethanol and the mixture was refluxed for 2 hours, then cooled to 20° C. The mixture was filtered, washed with isopropyl ether and dried to obtain 1.6 g of crude product which was purified by chromatography over silica. Elution with a methylene chloride and acetone mixture (95/5) yielded 1.5 g of 10β-[2-fluorobenzyl]-17α-(prop-1-ynyl)-Δ$^{4,9(11)}$-estradien-17β-ol-3-one melting at 212° C. and having an Rf=0.4 and a specific rotation of $[\alpha]_D = +12.5° \pm 2°$ (c=0.5% in chloroform).

Analysis: $C_{28}H_{31}FO_2$; molecular weight=418.53. Calculated: %C 80.35, %H 7.46, %F 4.53. Found 80.2, 7.6, 4.6.

In the chromatography, moreover, 0.130 g of 10β-[2-fluorobenzyl]-17α-(prop-1-ynyl)-Δ$^{9(11)}$-estraen-5α,17β-diol-3-one melting at 240° C. and with an Rf=0.25 were obtained.

EXAMPLE 13

10β-phenylthio-17α-(prop-1-ynyl)-Δ$^{4,9(11)}$-estradien-17β-ol-3-one

STEP A: 3,3-bismethoxy-10β-phenylthio-17α-(prop-1-ynyl)-Δ$^{9(11)}$-estraen-5α,17β-diol At −20° C., 63 ml of butyllithium in solution in hexane titrating 2.3M/l were introduced over 30 minutes into a solution of 15 ml of thiophenyl in 75 ml of tetrahydrofuran and the temperature was allowed to return to 20° C. over about 30 minutes to obtain the lithium derivative of thiophenol of the formula

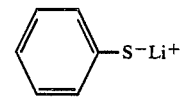

At 20° C., 12 g of the product comprising 50% of 3,3-bismethoxy-5α,10α-epoxy-17α-(prop-1-ynyl)-Δ$^{9(11)}$-estraen-17β-ol, 30% of 5β,10β-epoxide and 20% of 3,3-bismethoxy-17α-(prop-1-ynyl)-Δ$^{5(10),9(11)}$-estradien-17β-ol in 60 ml of tetrahydrofuran were added over about 30 minutes to the above lithium solution. The mixture was stirred for 2 hours at ambient temperature and the reaction mixture was introduced into an aqueous solution of ammonium chloride. The mixture was extracted with ethyl ether and the extracts were washed with water and concentrated to dryness by distillation under reduced pressure. The residue was chromatographed over silica and eluted with a methylene chloride, acetone and triethylamine mixture (95-5-0.1) to obtain 7.1 g of 3,3-bismethoxy-10β-phenylthio-17α-(prop-1-ynyl)-Δ$^{9(11)}$-estraen-5α,∫β-diol melting at 90°–95° C. and with a Rf=0.45 (product I).

Analysis: $C_{29}H_{38}O_4S$; molecular weight=482.688. Calculated: %C 72.16, %H 7.93, %S 6.64. Found: 72.2, 8.0, 6.5.

U.V. Spectrum (ethanol): Infl. 220 nm $E_1^1=192$, $\epsilon=9300$; Max. 267 nm $E_1^1=56$, $\epsilon=2700$.

In the chromatography, moreover, 2.25 g of 3,3-bismethoxy-10α-phenylthio-17α-(prop-1-ynyl)-Δ$^{9(11)}$-estraen-5β,17β-diol with an Rf=0.35 (product II) were obtained.

STEP B: 10β-phenylthio-17α-(prop-1-ynyl)-Δ$^{4,9(11)}$-estradien-17β-ol-3-one

At 40° C., 23 ml of a 2N aqueous hydrochloric acid solution were introduced into a solution of 5.6 g of the compound I of Step A in 56 ml of ethanol and the reaction mixture was refluxed for 90 minutes, then cooled and poured into a saturated aqueous sodium bicarbonate solution. The mixture was extracted with methylene chloride and the extracts were washed with water and concentrated to dryness by distillation under reduced pressure. The residue was chromatographed over silica and eluted with a methylene chloride-acetone mixture (95/5). After triturating in isopropyl ether, 2.6 g of 10β-phenylthio-17α-(prop-1-ynyl)-Δ$^{4,9(11)}$-estradien-17β-ol-3-one with an Rf=0.4 and melting at 180° C. were obtained.

Analysis: $C_{27}H_{30}O_2S$; molecular weight=418.603. Calculated: %C 77.47, TH 7.22, %S 7.65. Found: 77.3, 7.3, 7.5.

U.V. Spectrum (ethanol): Max. 224 nm $E_1^1=479$, $\epsilon=20,000$; Max. 248 nm $E_1^1=394$, $\epsilon=16,500$; Infl. 300 nm $E_1^1=51$, $\epsilon=2100$.

EXAMPLE 14

10β-[(4-dimethylamino-phenyl]-17α-(prop-1-ynyl)-Δ$^{4,9(11)}$-estradien-17β-ol-3-one STEP A: 3,3-ethylenedioxy-10β-[4-dimethylamino-phenyl]-Δ$^{9(11)}$-estraene-5α-ol-17-one The operation was the procedure of Step A of Example 7 of the European Pat. No. 0,057,115. A solution of 200 g of p-bromodimethylaminophenyl in 950 ml of tetrahydrofuran was introduced over 150 minutes into a mixture of 29 g of magnesium turnings in 50 ml of tetrahydrofuran while maintaining the temperature at 35° C. and the reaction was initiated by heating to 50° C. A mixture of 25 g of 3,3-ethylenedioxy-5α,10α-epoxy-Δ$^{9(11)}$-estraene-17-one in 500 ml of tetrahydrofuran and 757 mg of cuprous chloride was cooled to 5° C., and over 75 minutes, 284 ml of the above solution of 4-dimethylamino phenylmagnesium bromide were introduced dropwise. After stirring for 15 minutes, the mixture was poured into a liter of a saturated aqueous ammonium chloride solution and was extracted with ethyl acetate. The extracts were washed with a saturated ammonium chloride solution, then with a saturated sodium chloride solution, dried and evaporated to dryness under reduced pressure to obtain 46 g of crude product which was mainly 3,3-ethylenedioxy-11β-(dimethylamino-phenyl)-Δ$^{9(11)}$-estraen-5α-ol-17-one.

By chromatography over silica, the 10β-product was obtained which had the following Rf values:
Rf=0.28 (petroleum ether-ethyl acetate 5:5),
Rf=0.32 (petroleum ether-acetone 8:2),
Rf=0.36 (benzene-ethyl acetate 8:2).

STEP B: 3,3-ethylenedioxy-10β-[4-dimethylamino-phenyl]-17α-(prop-1-ynyl)-Δ$^{9(11)}$-estraen-5α,17β-diol Over 1 hour at +3° C., methyl acetylene was bubbled into 10 ml of 1N ethereal solution of magnesium ethyl bromide and 10 ml of tetrahydrofuran to obtain a solution of the desired magnesium methyl acetylene. Over 5 minutes, 1.13 g of 3,3-ethylenedioxy-10β-[4-dimethylamino-phenyl]-Δ$^{9(11)}$-estraen-5α,ol-17-one of Step A in solution in 10 ml of tetrahydrofuran were added to the above magnesium solution and the temperature was allowed to return to 20° C. After stirring for 2 hours, an aqueous ammonium chloride solution was added. After extracting with chloroform, washing with water, concentrating to dryness by distilling under reduced pressure, a residue was obtained which was chromatographed over silica and eluted with a benzene and ethyl acetate mixture (7/3) to obtain 0.295 g of 3,3-ethylenedioxy-10β-[4-dimethylamino-phenyl]-17α-(prop-1-ynyl)-Δ$^{9(11)}$-estraen-5α,17β-diol with a Rf=0.32 (product I).

During chromatography, moreover 0.810 g of 3,3-ethylenedioxy-10β-[4-dimethylamino-phenyl]-17,17-ethylenedioxy-Δ$^{9(11)}$-estraen-5α-ol melting at 212° C. (product II) were obtained.

STEP C: 10β-[4-dimethylamino-phenyl]-17α-(prop-1-ynyl)-Δ$^{4,9(11)}$-estradien-17β-ol-3-one 0.6 ml of a 2N aqueous hydrochloric acid solution were added at 20° C. while bubbling in argon to a solution of 0.295 g of compound I of Step A in 4 ml of ethanol, followed by stirring for 2 hours at ambient temperature. After alkalinizing by addition of sodium bicarbonate, extraction with methylene chloride was effected. The extracts were washed with water, dried and concentrated to dryness by distilling under reduced pressure. The residue was chromatographed over silica and eluted with a benzene-ethyl acetate mixture (9/1) to obtain 0.210 g of 10β-[4-dimethylamino-phenyl]-17α-(prop-1-ynyl)-Δ$^{4,9(11)}$-estradien-17β-ol-3-one with an Rf=0.13.

Analysis: $C_{29}H_{35}NO_2$; molecular weight=429.58. Calculated: %C 81.08, %H 8.21, %N 3.26. Found: 81.1, 8.5, 3.1.

U.V. Spectrum (ethanol): Infl. 246 nm $E_1^1=510$; Max. 259 nm $E_1^1=576$, $\epsilon=24700$; Max. 297 nm $E_1^1=61$, $\epsilon=2600$.

EXAMPLE 15

10β-[4-methyl-benzyl]-17α-(prop-1-ynyl)-Δ$^{4,6,9(11)}$-estratrien 17β-ol-3-one

A suspension of 4 g of 10β-[4-methyl-benzyl]-17α-prop-1-ynyl)-Δ$^{4,9(11)}$-estradien-17β-ol-3-one of Example 4, 80 ml of ethanol, 12 ml of ethyl orthoformate and 16 mg of p-toluene sulfonic acid was stirred for an hour at ambient temperature and then 3 ml of triethylamine were added. Stirring was continued for 5 minutes and then the mixture was poured into 100 ml of an aqueous solution of sodium bicarbonate, agitated for 15 minutes and then extracted with dichloromethane. The pH was made alkaline by addition of 2 ml of triethylamine. After drying and concentrating the mixture to dryness, 6.5 g of a colorless oil were obtained.

The said oil was added to a solution of 2.64 g of chloranile in 100 ml of acetone with 5% of water and after an hour of reaction, 100 ml of 10% sodium thiosulfate and 100 ml of sodium bicarbonate solution were introduced. After stirring for an hour and extracting the aqueous phase with dichloromethane, 4.8 g of crude product were obtained which was chromatographed over silica [eluent: petroleum ether (b.p. 60°–80° C.)-ethyl acetate 7:3] to obtain 3.341 g of white mousse, The latter was crystallized from ethyl acetate and the crystallized product was collected, washed with cooled ethyl acetate, then with petroleum ether (b.p. 60°–80° C.), dried at 50° C. under reduced pressure to obtain 2.142 g of 10β-[4-methyl-benzyl]-17α-(prop-1-ynyl)-Δ$^{4,6,9(11)}$-estratrien-17β-ol-3-one melting at 202°λC. and with an Rf=0.17.

Analysis: $C_{29}H_{32}O_2$; molecular weight=412.57, Calculated: %C, 84.43, %H 7.82. Found: 84.7, 7.9.

EXAMPLE 16

6-methylene-10β-[4-methyl-benzyl]-17α-propynyl-Δ$^{4,9(11)}$-estradien-17β-ol-3-one 102 ml of formaldehyde diethylacetal, 13 ml of phosphorus oxychloride and 3 g of the product of Example 4 were added to a solution of 3.6 g of sodium acetate in 102 ml of chloroform and the mixture was heated to 80° C. for 40 minutes and cooled in an ice bath containing methanol. Then sodium carbonate was slowly added followed by 100 ml of water. After extracting with chloroform, concentrating under reduced pressure, purifying by chromatography over silica (eluent: cyclohexane-ethyl acetate 8-2), 627 mg of 6-methylene-10β-[4-methyl-benzyl]-17α-propynyl-Δ$^{4,9(11)}$-estradien-17β-ol-3-one with a melting point of 188° C. after crystallization from ether were obtained.

Analysis: $C_{30}H_{34}O_2$; molecular weight=426.60. Calculated: %C 84.47, %H 8.03. Found: 84.2, 8.1.

EXAMPLE 17

6-methyl-10β-[4-methyl-benzyl]-17α-propynyl-Δ$^{4,6,9(11)}$-estratrien-17β-ol-3-one STEP A: 17β-cyano-10β-[4-methyl-benzyl]-Δ$^{4,9(11)}$-estradien-17α-ol-3-one 20 g of 3,3-ethylenedioxy-5α,10α-epoxy-17α-trimethylsilyloxy-17β-cyano-Δ$^{9(11)}$-estraene prepared as in French Pat. No. 2,082,129 in solution in 100 ml of tetrahydrofuran were added to 250 ml of 0.75M tetrahydrofuran solution of α-chloro-xylene magnesium cooled to +14° C. After allowing the temperature to return to ambient, the mixture was poured into an iced aqueous ammonium chloride solution and was extracted with methylene chloride. After drying, the solvent was evaporated to obtain 37.7 g of crude product. The crude product was dissolved in 500 ml of ethanol and 100 ml of 5N hydrochloric acid and the mixture was refluxed for 1 hour, then cooled and filtered. The crystallized product was washed with ethanol and dried at 70° C. under reduced pressure to obtain 13.6 g of 17β-cyano-10β-[4-methyl-benzyl]-Δ$^{4,9(11)}$-estradien-17α-ol-3-one melting at 234° C.

STEP B: 17β-cyano-6-methylene-10β-[4-methyl-benzyl]-Δ$^{4,9(11)}$-estradien-17α-ol-3-one 8 g of the product of Step A were added to a solution of 9.3 g of sodium acetate, 282 ml of formaldehyde diethylacetal, 282 ml of chloroform and 34.5 g of phosphorus oxychloride. After heating for 45 minutes at 70° C., the mixture was cooled to ambient temperature and poured into an iced aqueous saturated sodium bicarbonate solution. The mixture was stirred for 45 minutes and then was extracted with chloroform. After concentrating the organic phase to dryness, the residue was chromatographed over silica (eluent: cyclohexane-ethyl acetate 6-4) and the residue was concreted in ether to obtain 2 g of 17β-cyano-16-methylene-10β-[4-methyl-benzyl]-Δ$^{4,9(11)}$-estradien-17α-ol-3-one melting at 216° C.

STEP C: 17β-cyano-6-methyl-10β-[4-methyl-benzyl]-Δ$^{4,6,9(11)}$-estratrien-17α-ol-3-one 2.5 g of the product of Step B and 1.5 g of active carbon with 5% of palladium in 100 ml of ethanol were refluxed while adding over 2 hours 100 ml of ethanol containing 5% of benzyl alcohol. The reaction mixture was cooled, the catalyst was filtered off and the solvents were evaporated under reduced pressure. The residue was purified by chromatography over silica (eluent: n-hexane ethyl-acetate 7-3) to obtain 2.42 g of 17β-cyano-6-methyl-10β-[4-methyl-benzyl]-Δ$^{4,6,9(11)}$-estratrien-17α-ol-3-one used as is for the next step.

STEP D: 3,3-ethylenedioxy-6-methyl-10β-[4-methyl-benzyl]-Δ$^{4,6,9(11)}$-estratrien-17-one 2.4 g of the product of Step C in 150 ml of benzene with 70 mg of p-toluene sulfonic acid and 11 ml of ethylene glycol were refluxed for 4 hours. The volume was concentrated to a quarter and the mixture was cooled to ambient temperature, 10 ml of washing soda and 50 ml of ethanol were added and the mixture was stirred for 2 hours. After diluting with 100 ml of water and extracting with methylene chloride, the solvents were eliminated. The residue was purified by chromatography over silica (eluent: n-hexane-ethyl acetate 7-3 with 1% of triethylamine) to obtain 1.86 g of 3,3-ethylenedioxy-6-methyl-10β-[4-methyl-benzyl]-Δ$^{4,6,9(11)}$-estratrien-17-one.

STEP E: 6-methyl-10β-[4-methyl-benzyl]-17α-propynyl-Δ$^{4,6,9(11)}$-estratrien-17β-ol-3-one 50 ml of tetrahydroguran were added to 17 ml of a 1M/1 butyllithium hexane solution and the mixture was cooled to −70° C. and submitted to bubbling in of methylacetylene for 30 minutes. After stirring for 30 minutes, 1.5 g of the product of Step D in 2 ml of tetrahydrofuran were added. The temperature was allowed to return to ambient and the mixture was left for 2 hours while stirring. The reaction medium was poured into an iced aqueous ammonium chloride solution and was extracted with ethyl acetate. After concentrating the extract to dryness, the residue was taken up in a mixture of 2 ml of 2N hydrochloric acid and 10 ml of ethanol and stirred for 90 minutes. 1.5 g of crude product were recovered which was purified by chromatographed over silica (eluent: n-hexane-ethyl acetate 7-3) to obtain 612 mg of 6-methyl-10β-[4-methyl-benzyl]-17α-propynyl-Δ$^{4,6,9(11)}$-estratrien-17β-ol-3-one with a specific rotation of $[\alpha]_D = -175° \pm 3°$ (c=0.5% in CHCl$_3$).

EXAMPLE 18

10β-[4-methylbenzyl]-17α-(3-hydroxy-1-propynyl)-Δ$^{4,9(11)}$-estradien-17β-ol-3-one STEP A: 3,3-ethylenedioxy-17β-cyano-17α-trimethyl-silyloxy-10β-[4-methylbenzyl]-Δ$^{9(11)\text{-}estraene}$-5α-ol and 3,3-ethylene-dioxy-17β-cyano-17α-trimethylsilyloxy-10α-[4-methylbenzyl]-Δ$^{9(11)}$-estraene-5β-ol in the form of a mixture.

Using the procedure of Step A of Example 17, 37.4 g of 3,3-ethylene-dioxy-5,10-epoxy-17α-trimethylsilyloxy-17β-cyano-Δ$^{9,(11)}$-estrene in the form of a mixture of 5α,10α-isomer and 5β,10β-epoxy isomer were reacted to obtain 67 g of crude 3,3-ethylenedioxy-17β-cyano-17α-trimethyl-silyloxy-10β-[4-methylbenzyl]-Δ$^{9(11)}$-estraene-5α-ol and 3,3-ethylene-dioxy-17β-cyano-17α-trimethylsilyloxy-10α-[4-methylbenzyl]-Δ$^{9(11)}$-estraene-5β-ol in the form of a mixture of isomers used as is for the following step.

STEP B: 3,3-ethylenedioxy-10β-[4-methylbenzyl]-Δ$^{9(11)}$-estraene-5α-ol-17-one and 3,3-ethylenedioxy-10α-[4-methylbenzyl]-Δ$^{9(11)}$-estraene-5β-ol-17-one 70 ml of washing soda were added to a solution of 58.15 g of the product of Step A in 2.4 ml of ethanol and after stirring for 30 minutes, the solvent was evaporated under reduced pressure at 35°–40° C. Water was added and the mixture was extracted with methylene chloride. The organic phase was washed with water, then with a saturated sodium chloride solution, dried and concentrated to dryness to obtain 44.4 g of crude product. The 2 isomers were isolated by chromatography over silica (eluent: petroleum ether (b.p.=40°–70° C.)-ethyl acetate 7-3 with 1°/$_{oo}$ of triethylamine) and after crystallization of the different fractions from isopropyl ether, 18.6 g of 5α-hydroxy-10β-[4-methylbenzyl]-isomer and 3.66 g of 5β-hydroxy-10α-[4-methylbenzyl]-isomer were obtained.

STEP C: 3,3-ethylenedioxy-10β-[4-methyl-benzyl]-17α-[3-(2-tetrahydropyranyloxy)-1-propynyl]-Δ$^{9(11)}$-estraene-5α,17β-diol and isomer 5β-hydroxy-10α-[4-methyl-benzyl].

2.2 g of tetrahydropyan ether of propargyl alcohol in solution in 80 ml of ether were added over 20 minutes to 9.4 ml of a 1.6M/1 ethereal solution of methyllithium cooled to +10° C. and then the temperature was allowed to return to ambient. 874 mg of the product of Step B were added to the suspension of the lithium derivative prepared above and the mixture was stirred for 7 hours at ambient temperature. The reaction mixture was poured into a saturated aqueous solution of iced ammonium chloride and was extracted with ethyl acetate. The organic phase was washed with a saturated aqueous sodium chloride solution, dried and concentrated to dryness under reduced pressure. The residue was chromatographed over silica and eluted with cyclohexane-ethyl acetate (6-4) with 1°/$_{oo}$ of triethylamine to obtain 860 mg of product in the form of 5α-hydroxy-10β-[4-methyl benzyl] isomer as well as 80 mg of 5β-hydroxy-10α-[4-methylbenzyl]isomer.

STEP D: 10β-[4-methylbenzyl]-17α-(3-hydroxy-1-propynyl)-Δ$^{4,9(11)}$-estradien-17β-ol-3-one A solution of 1.7 g of product in the form 5α-hydroxy-10β-[4-methylbenzyl] isomer of Step C, 30 ml of ethanol and 7.5 ml of 5N hydrochloric acid was heated for 1 hour at 50° C. and the reaction mixture was poured into iced water, made alkaline with concentrated ammonia and was extracted with ethyl acetate. The organic phase was washed with water, then with a saturated aqueous sodium chloride solution, dried and concentrated to dryness under reduced pressure to obtain 1.3 g of crude product which was crystallized from methylene chloride to obtain 10β-[4-methylbenzyl]-17α-(3-hydroxy-1-propynyl)-Δ$^{4,9(11)}$-estradien-17β-ol-3-one melting at 213° C. and having a specific rotation of $[α]_D = +13° ± 1°$ (c = 1% in CHCl$_3$).

Analysis: C$_{29}$H$_{34}$O$_3$; molecular weight = 430.59. Calculated: %C 79.95, %H 7.87, %Cl 1.17. Found: 80.0, 7.9, 1.2.

EXAMPLE 19

21-chloro-10β-[4-methylbenzyl]-19-nor-17α-Δ$^{4,9(11)}$-pregnadien-20-yn-17β-ol-3-one STEP A: 3,3-ethylenedioxy-21-chloro-10β-[4-methylbenzyl]-19-nor-20-yn-17α-Δ$^{9(11)}$-pregnaene-5α,17β-diol 3.3 ml of an 0.003M ethereal solution of phenyllithium were added over 3 minutes to 5.5 ml of ether cooled to 5° C. and then over 6 minutes, 0.12 ml of trans 1,2-dichloroethylene was added keeping the temperature below 10° C. The temperature was allowed to return to ambient and the mixture was agitated for 40 minutes to obtain a suspension of lithium chloroacetylide. 0.218 g of 3,3-ethylene-dioxy-10β-[4-methylbenzyl]-Δ$^{9(11)}$-estraen-5α-ol-17-one of Step B of Example 18 in solution in 2.2 ml of tetrahydrofuran were added to the above suspension and the mixture was stirred at ambient temperature for 16 hours. 5.5 ml of a saturated aqueous solution of ammonium chloride were added and after stirring for 10 minutes, decanting, extracting with ethyl acetate, washing the organic phase with a saturated aqueous solution of sodium chloride, drying and evaporating to dryness, the residue was chromatographed over silica [eluent: petroleum ether (b.p.: 40°-70° C.)-ethyl acetate with 1°/$_{oo}$ triethylamine] to obtain 0.194 g of 3,3-ethylenedioxy-21-chloro-10β-[4-methylbenzyl]-19-nor-20-yn-17α-Δ$^{9(11)}$-pregnaene-5α,17β-diol.

STEP B: 21-chloro-10β-[4-methylbenzyl]-19-nor-17α-Δ$^{4,9(11)}$-pregnadien-17β-ol-20-yn-3-one 42 ml of 50% hydrochloric acid were added to a solution of 3.5 g of product of Step A and 105 ml of ethanol and after heating for 4 hours at 55° C., cooling the reaction mixture, adding water and then 20 ml of concentrated ammonia, separating, washing with water, drying and concentrating to dryness under reduced pressure at 50° C., 2.62 g of 21-chloro-10β-[4-methylbenzyl]-19-nor-17α-Δ$^{4,9(11)}$-pregnadien-17β-ol-20-yn-3-one melting at 254° C. and having a specific rotation of $[α]_D = +13° ± 1°$ (c = 1% in CHCl$_3$) were obtained.

Analysis: C$_{28}$H$_{31}$ClO$_2$; molecular weight = 435.01. Calculated: %C, 77.31, %H 7.18, %Cl 8.14. Found: 77.3, 7.3, 8.3.

PHARMACOLOGICAL STUDY (1) Study of the activity on the hormone receptors
Progestogen receptor of rabbit uterus Impuberal rabbits of about 1 kg received a cutaneous application of 25 g of estradiol and 5 days after this treatment, the animals were killed. Their uterus were removed, weighed and homogenized at 0° C. using a Potter teflon-glass in a TS buffered solution (Tris 10 mM, saccharose 0.25M, HCl pH 7.4) (1 g of tissue for 50 ml of TS). The homogenate was then ultracentrifuged at 105,000 g for 90 minutes at 0° C. Aliquots of the supernatant so obtained were incubated at 0° C. for a time t, with a constant concentration (T) of Product R tritiated (17,21-dimethyl-19-nor-Δ$^{4,9}$-pregnadiene-3,20-dione) in the presence of increasing concentrations (0–2,500 10$^{-9}$M) either of R cold, or of cold progesterone, or of the cold product under test. The concentration of tritiated R bonded (B) was then measured in each incubate by the technique of adsorption to dextran-carbon.

Glucocorticoid receptor of rat thymus:

Male Sprague-Dawley EOPS rats of 160–200 g were suprarenalectomized and 4–8 days after this excision, the animals were killed. Their thymus was removed and homogenized at 0° C. in a buffer Tris 10 mM saccharose 0.25M, dithiotreitol 2 mM, HCl pH 7.4, using a Potter polytetrafluoroethylene-glass (1 g of tissue for 10 ml of TS). The homogenate was then ultracentrifuged at 105,000 g for 90 minutes at 0° C. Aliquots of the supernatant so obtained were incubated at 0° C. for a time (t) with a constant concentration (T) of tritiated dexamethasone in the presence of increasing concentrations (0–2,500.10$^{-9}$M) either of cold dexamethasone, or of the cold product under test. The concentration of tritiated dexamethasone bonded (B) was then measured in each incubate by the technique of adsorption to dextran-carbon.

Calculation of the relative liaison affinity

The calculation of the relative liaison affinity (RLA) was identical for all the receptors. The two following curves were traced: the percentage of tritiated hormone bonded B as a function of the logarithm of the concentration of the cold reference hormone, and B/T as a function of the logarithm of the concentration of the cold product under test. The straight line was determined of the equation $$I_{50} = \frac{\left(\frac{B}{T} \max + \frac{B}{T} \min \right)}{2}.$$

(B/T) max = percentage of tritiated hormone bonded for an incubation of this tritiated hormone at the concentration (T).

(B/T) min. = percentage of tritiated hormone bonded for an incubation of the tritiated hormone at the concentration (T) in the presence of a great excess of cold hormone (2500.10$^{-9}$M).

The intersections of the straight line $I_{50}$ and of the curves enabled the concentrations of the cold reference hormone (CH) and the cold product under test (CX) to be evaluated which inhibit by 50% the bonding of the tritiated hormone on the receptor.

The relative liaison affinity (RLA) of the product under test was determined by the equation $$RLA = 100 \frac{(CH)}{(CX)}$$

and the following results were obtained:

| Product of Example | Incubation time at 0° C. | | | |
|---|---|---|---|---|
| | Progestogen | | Glucocorticoid | |
| | 2 H | 24 H | 4 H | 24 H |
| 1 | 0.1 | 0.1 | 160 | 57 |
| 4 | 0.2 | 0.2 | 125 | 128 |
| 7 | 0.4 | 0.1 | 226 | 112 |
| 10 | 0.9 | 0.5 | 218 | 152 |
| 12 | 0.1 | 0.1 | 136 | 45 |

CONCLUSION

The products of Examples 1,4,7,10 and 12 presented a very marked affinity for the glucocorticoid receptors as well as a negligible activity for the progestogen receptor. From the reesults obtained, it can be concluded tha the products can present agonist or antagonist activities of the glucocorticoids, while being deprived of progestomimetic or anti-progestomimetic activity.

(II). Anti-glucocorticoid activity

The technique utilized envolved from the method described by Dausse et al in "Molecular Pharmacology", Vol. 13, p. 948–955 (1977) ("the relationship between glucocorticoid structure and effects upon Thymocytes") for the thymocytes of mice. Thymocytes of suprarenalectomized rats were incubated at 37° C. for 3 hours in a nutritive medium containing $5.10^{-8}M$ of dexamethasone in the presence or not of a product under study at different concentrations. Tritiated uridine was added and the incubation was continued for one hour. The incubates were cooled, then treated with a 5% solution of trichloroacetic acid, filtered on Whatman paper GF/A, and washed three times with a 5% solutioh of trichloroacetic acid. The radio-activity retained by the filter was determined. The glucocorticoids and in particular dexamethasone caused a diminution in the incorporation of tritiated uridine. The products of Examples 1,4,7,10 and 12 oppose this effect.

| Product of Example | $5 \cdot 10^{-8}$ dexamethasone + product under test at a concentration of: | % inhibition of the effect of Dexamethasone |
|---|---|---|
| 1 | $10^{-8}$ M | 20 |
| | $10^{-7}$ M | 55 |
| | $10^{-6}$ M | 80 |
| 4 | $10^{-8}$ M | 10 |
| | $10^{-7}$ M | 30 |
| | $10^{-6}$ M | 83 |
| 7 | $10^{-8}$ M | 10 |
| | $10^{-7}$ M | 16 |
| | $10^{-6}$ M | 65 |
| 12 | $10^{-8}$ M | 6 |
| | $10^{-7}$ M | 12 |
| | $10^{-6}$ M | 67 |

CONCLUSION

The products studied presented a very marked anti-glucocorticoid activity, while being deprived, for the most part, of glucocorticoid activity.

Pharmaceutical compositions:

Tablets were prepared containing 50 mg of the product of Example 1 and sufficient excipient of talc, starch, magnesium stearate for a tablet of 120 mg.

Various modifications of the products and methods of the invention may be made without departing from the spirit or scope thereof and it is to be understood that the invention is intended to be limited only as defined in the appended claims.

What is claimed is:

1. A steroid of the formula

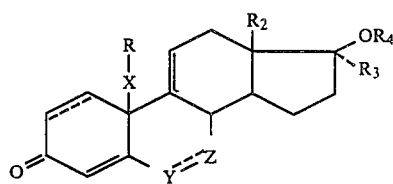

wherein X is methylene and R is an optionally substituted phenyl, naphthyl, furyl, thienyl, pyrolyl, oxazolyl, thiazolyl, imidazolyl, pyrazolyl, thiadiazolyl, triazolyl, oxadiazolyl, tetrazolyl, pyridinyl, pyrazinyl, pyrimidinyl or optionally substituted vinyl or ethynyl or X is a simple bond or —S— and R is optionally substituted phenyl, naphthyl, furyl, thienyl, pyrolyl, oxazolyl, thiazolyl, imidazolyl, pyrazolyl, thiadiazolyl, triazolyl, oxadiazolyl, tetrazolyl, pyridinyl, pyrazinyl, pyrimidinyl, $R_2$ is methyl or ethyl, $R_3$ is selected from the group consisting of optionally substituted alkyl of 2 to 8 carbon atoms and optionally substituted alkenyl and alkynyl of 2 to 8 carbon atoms, $R_4$ is selected from the group consisting of hydrogen and acyl,

is selected from the group consisting of

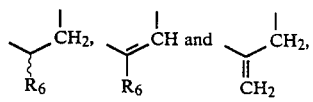

$R_6$ is selected from the group consisting of hydrogen and methyl, the wavy line indicates $\alpha$ or $\beta$- and the dotted line in 1(2) indicates the optional presence of a second carbon-carbon bond, the optional substitutents being selected from the group consisting of alkyl, alkoxy and alkylthio of 1 to 4 carbon atoms, alkenyl and alkynyl of 2 to 4 carbon atoms, halogen, haloalkyl of 1 to 4 carbon atoms, —NH$_2$, protected —NH$_2$, monoalkylamino and dialkylamino of 1 to 4 carbon atoms, —OH, protected —OH, —SH, —COOH, esterified or salified COOH, carbamoyl, —NO$_2$, aminoalkyl, monoaminoalkyl and dialkylaminoalkyl of 1 to 4 alkyl carbon atoms, hydroxyalkyl of 1 to 4 carbon atoms and carboxyalkyl of 1 to 4 carbon atoms.

2. A steroid of claim 1 wherein R is selected from the group consisting of phenyl, pyridyl and phenyl substituted with at least one member of the group consisting of alkyl and alkoxy of 1 to 4 carbon atoms, halogen, amino and dialkylamino of 1 to 4 alkyl carbon atoms.

3. A steroid of claim 1 wherein R is selected from the group consisting of vinyl, methylvinyl and ethynyl optionally substituted with a member of the group consisting of alkyl of 1 to 4 carbon atoms, phenyl, carboxy, esterified carboxy, hydroxymethyl, amino, alkylamino of 1 to 4 carbon atoms and protected amino.

4. A steroid of claim 1 selected from the group consisting of 10β-benzyl-17α-(prop-1-ynyl)-Δ$^{4,9(11)}$-estradien-17β-ol-3-one, 10β-[4-methyl-benzyl]-17α-(prop-1-ynyl)-Δ$^{4,9(11)}$-estradien-17β-ol-3-one, 10β-(2-methyl-prop-2-en-1-yl)-17α-(prop-1-ynyl)-Δ4,9(11)-estradien-17β-ol-3-one, 10β-[(4-methoxyphenyl)-thio]-17α-(prop-1-ynyl)-Δ$^{4,9(11)}$-estradien-17β-ol-3-one and 10β-[2-fluoro-benzyl]-17α-(prop-1-ynyl)-Δ$^{4,9(11)}$-estradien-17β-ol-3-one.

5. An anti-glucocorticoid composition comprising an anti-glucocorticoidally effective amount of at least one compound of claim 1 and an inert pharmaceutical carrier.

6. A composition of claim 5 wherein R is selected from the group consisting of phenyl, pyridyl and phenyl substituted with at least one member of the group consisting of alkyl and alkoxy of 1 to 4 carbon atoms, halogen, amino and dialkylamino of 1 to 4 alkyl carbon atoms.

7. A composition of claim 5 wherein R is selected from the group consisting of vinyl, methylvinyl and ethynyl optionally substituted with a member of the group consisting of alkyl of 1 to 4 carbon atoms, phenyl, carboxy, esterified carboxy, hydroxymethyl, amino, alkylamino of 1 to 4 carbon atoms and protected amino.

8. A composition of claim 5 selected from the group consisting of 10β-benzyl-17α-(prop-1-ynyl)-Δ$^{4,9(11)}$-estradien-17β-ol-3-one, 10β-[4-methyl-benzyl]-17α-(prop-1-ynyl)-Δ$^{4,9(11)}$-estradien-17β-ol-3-one, 10β-(2-methylprop-2-en-1-yl)-17α-(prop-1ynyl)-Δ$^{4,9(11)}$-estradien-17β-ol-3-one, 10β-[(4-methoxyphenyl)-thio]-17α-(prop-1-ynyl)-Δ$^{4,9(11)}$-estradien-17β-ol-3-one and 10β-[2-fluoro-benzyl]-17α-(prop-1-ynyl)-Δ$^{4,9(11)}$-estradien-17β-ol-3-one.

9. A method of inducing antiglucocorticoid activity in warm-blooded animals comprising administering to warm-blooded animals an antiglucocorticoidally effective amount of at least one compound of claim 1.

10. A method of claim 9 wherein in the compound R is selected from the group consisting of phenyl, pyridyl and phenyl substituted with at least one member of the group consisting of alkyl and alkoxy of 1 to 4 carbon atoms, halogen, amino and dialkylamino of 1 to 4 alkyl carbon atoms.

11. A method of claim 9 wherein in the compound R is selected from the group consisting of vinyl, methylvinyl and ethynyl optionally substituted with a member of the group consisting of alkyl of 1 to 4 carbon atoms, phenyl, carboxy, esterified carboxy, hydroxymethyl, amino, alkylamino of 1 to 4 carbon atoms and protected amino.

12. A method of claim 9 wherein the compound is selected from the group consisting of 10β-benzyl-17α-(prop-1-ynyl)-Δ$^{4,9(11)}$-estradien-17β-ol-3-one, 10β-[4-methyl-benzyl]-17α-(prop-1-ynyl)-Δ$^{4,9(11)}$-estradien-17β-ol-3-one, 10β-(2-methylprop-2-en-1-yl)-17α-(prop-1-ynyl)-Δ$^{4,9(11)}$-estradien-17β-ol-3-one, 10β-[(4-methoxyphenyl)-thio]-17α-(prop-1-ynyl)-Δ$^{4,9(11)}$-estradien-17β-ol-3-one and 10β-[2-fluoro-benzyl]-17α-(prop-1-ynyl)-Δ$^{4,9(11)}$-estradien-17β-ol-3-one.

13. A compound of the formula

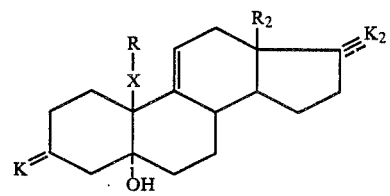

wherein X is methylene and R is an optionally substituted phenyl, naphthyl, furyl, thienyl, pyrolyl, oxazolyl, thiazolyl, imidazolyl, pyrazolyl, thiadiazolyl, triazolyl, oxadiazolyl, tetrazolyl, pyridinyl, pyrazinyl, pyrimidinyl or optionally substituted vinyl or ethynyl or X is a simple bond or —S— and R is optionally substituted phenyl, naphthyl, furyl, thienyl, pyrolyl, oxazolyl, thiazolyl, imidazolyl, pyrazolyl, thiadiazolyl, triazolyl, oxadiazolyl, tetrazolyl, pyridinyl, pyrazinyl, pyrimidinyl, $R_2$ is methyl or ethyl, K is a ketoprotective group and $K_2$ is selected from the group consisting of a ketone, a protective ketone and

wherein $R_3$ is selected from the group consisting of optionally substituted alkyl of 2 to 8 carbon atoms and optionally substituted alkenyl and alkynyl of 2 to 8 carbon atoms and the OH may contain a protective group: the optional substituents being selected from the group consisting of alkyl, alkoxy and alkylthio of 1 to 4 carbon atoms, alkenyl and alkynyl of 2 to 4 carbon atoms, halogen, haloalkyl of 1 to 4 carbon atoms, —NH$_2$, protected —NH$_2$, monoalkylamino an dialkylamino of 1 to 4 carbon atoms, —OH, protected —OH, —SH, —COOH, esterified or salified COOH, carbamoyl, —NO$_2$, aminoalkyl, monoaminoalkyl and dialkylaminoalkyl of 1 to 4 alkyl carbon atoms, hydroxyalkyl of 1 to 4 carbon atoms and carboxyalkyl of 1 to 4 carbon atoms.

* * * * *